Aug. 2, 1966 L. K. OKU Plant Pat. 2,660
CARNATION
Filed March 19, 1965
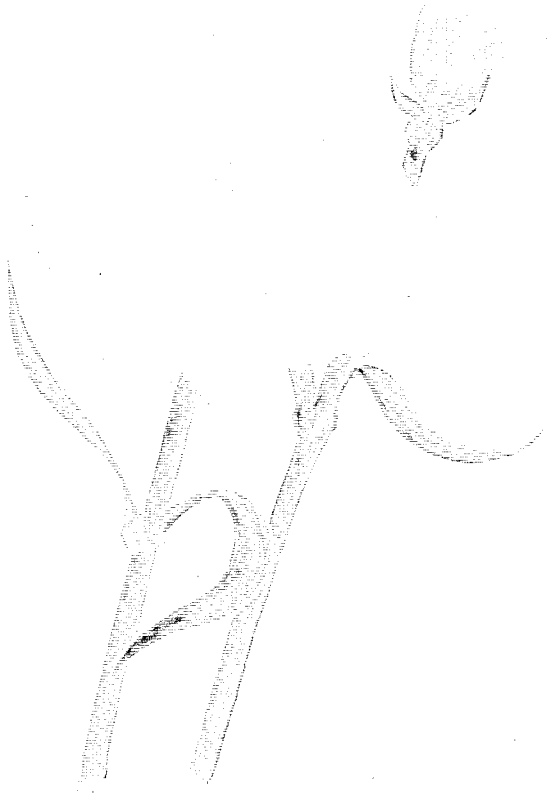
INVENTOR.
Leonard K. Oku
BY Flehr and Swain
Attorneys United States Patent Office Plant Pat. 2,660
Patented August 2, 1966

2,660
CARNATION
Leonard K. Oku, 300 N. Bailey Ave.,
Mountain View, Calif.
Filed Mar. 19, 1965, Ser. No. 441,386
1 Claim. (Cl. Plt.—70)

This invention relates to a carnation and more particularly to a carnation which has a flower having unique color characteristics.

This new carnation is from an unnamed sport which has a substantially uniform color of pale green. The parentage of this unnamed sport is Elliott's Improved White Sim (unpatented) registered with the American Carnation Society on February 17, 1954, the patent of which is the William Sim Carnation described in Plant Patent No. 669 issued on January 15, 1946.

Since the color break was first observed many hundreds of cuttings have been planted.

Asexual propagation of the newly discovered carnation was made at Mountain View, California, by taking cuttings in the years 1960 through 1964 and growing them. Cuttings so taken and grown have consistently produced flowers with blossoms having the new and distinctive color hereinafter described more in detail.

In the drawing there are illustrated two separate blossoms in full bloom on two stalks and a petal from a blossom.

The following is a detailed description of the new carnation.

The description of the carnation in United States Letters Patent No. 669 and the description of Elliot's Improved White Sim carnation are applicable to the newly discovered variety with one exception; namely, the color of the flower.

The petals of the flower have a substantially uniform color with the exception that the bases of the petals may have a slightly darker shade of the color at the base. The color of the petal field closely approximates the color shown in Plate 30, Swatches A3 and A4 of the Reinhold Color Atlas by A. Kornerup and J. H. Wanscher published by Reinhold Publishing Corporation, New York, New York (Library of Congress Catalogue No. 62–8756). The closest descriptive term for the color of the flower is pale green, identified as 30 A3 in the above named color atlas.

I claim:

The new and distinct variety of carnation substantially as herein described and illustrated.

No references cited.

ANTONIO F. GUIDA, *Acting Primary Examiner.*

R. E. BAGWILL, *Assistant Examiner.*